(12) United States Patent
Kozersky

(10) Patent No.: US 6,932,780 B2
(45) Date of Patent: Aug. 23, 2005

(54) ORTHOSIS FOR SUPPORTING SPINAL STRUCTURES

(76) Inventor: David J. Kozersky, 2627 Haverford Rd., Columbus, OH (US) 43220

( * ) Notice: Subject to any disclaimer, the term of this patent is extended or adjusted under 35 U.S.C. 154(b) by 0 days.

(21) Appl. No.: 10/853,428

(22) Filed: May 25, 2004

(65) Prior Publication Data

US 2004/0220503 A1 Nov. 4, 2004

Related U.S. Application Data

(63) Continuation-in-part of application No. 10/353,686, filed on Jan. 29, 2003, now Pat. No. 6,840,916.

(51) Int. Cl.$^7$ .................................................. A61F 5/00
(52) U.S. Cl. .............................. 602/19; 602/5; 128/874
(58) Field of Search ............... 602/5, 19; 128/869–876, 128/845, 846

(56) References Cited

U.S. PATENT DOCUMENTS

| | | |
|---|---|---|
| 5,362,304 A | 11/1994 | Varn |
| 5,564,788 A | 10/1996 | Warhaftig |
| 5,718,670 A | 2/1998 | Bremer |
| 5,853,378 A | 12/1998 | Modglin |
| 5,967,998 A | 10/1999 | Modglin |
| 6,126,660 A | 10/2000 | Dietz |
| 6,213,968 B1 | 4/2001 | Heinz et al. |

Primary Examiner—Michael A. Brown
(74) Attorney, Agent, or Firm—Francis T. Kremblas, Jr.; Kremblas, Foster, Phillips & Pollick

(57) ABSTRACT

A spinal orthosis having discrete left and right side belt-like segments configured to wrap around a wearer's torso and be adjustably connected in the front and rear portions of the side segments. Each belt-like segment includes an anterior and posterior edges disposed in overlapping relationship to one another. Fastening means are provided for releasably connecting the anterior overlapping portions to initially mount the orthosis around the wearer's waist. The posterior portion of the orthosis includes a semi-rigid or rigid lumbar support panel to which the overlapping posterior portions of each side segment are adjustably connected via a plurality of slots and aligned holes in either the panel or the side segments and a fastener extended through a respective aligned hole and slot. The fasteners are permitted to slide within the confines of the respective slots to modify the effective circumferential girth defined by the side segments. A pair of straps are attached to the posterior end portions of each segment and extend in opposing directions for releasably fixing to a frontal portion of a belt-like segment to permit the wearer to increase or decrease the compressive forces applied by the orthosis.

2 Claims, 14 Drawing Sheets

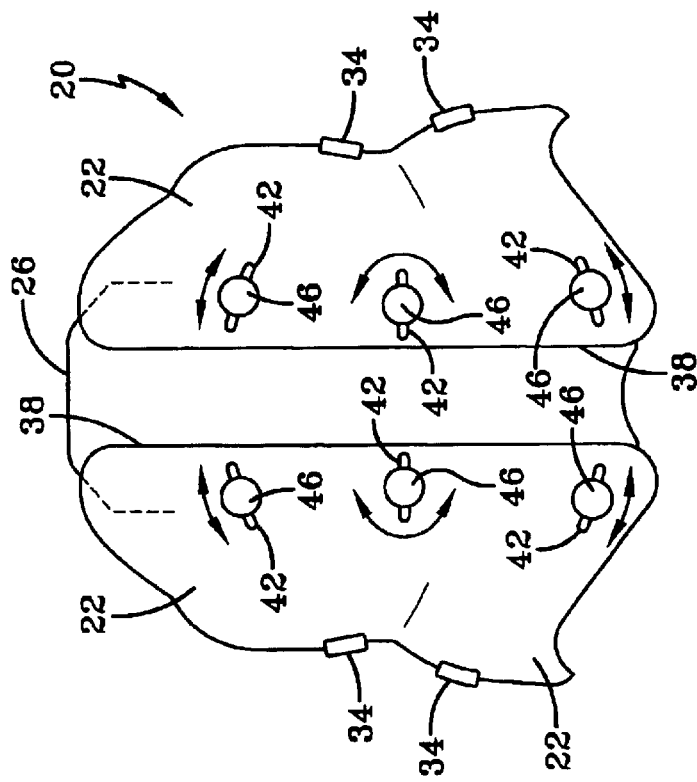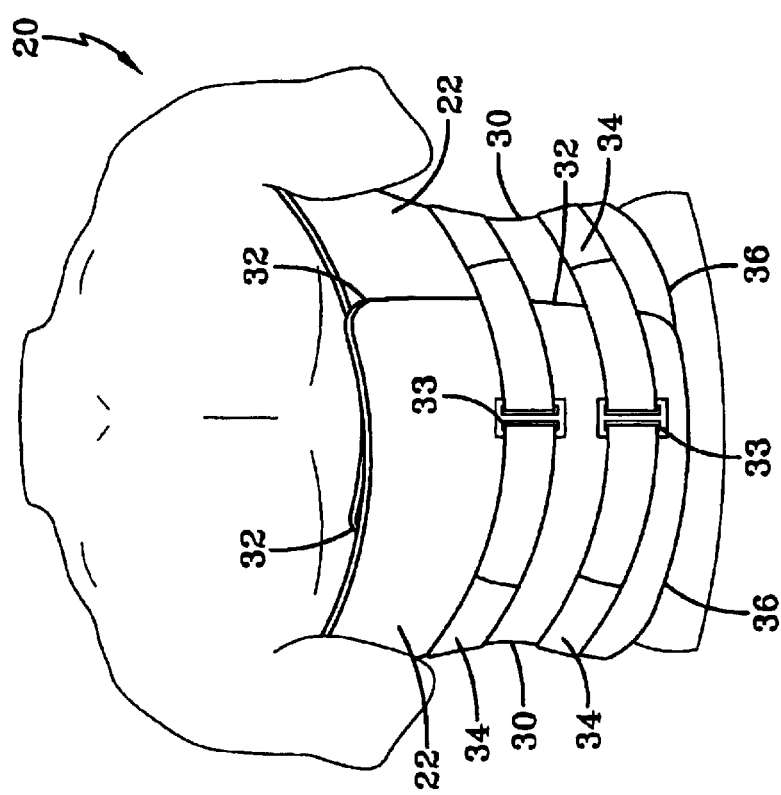

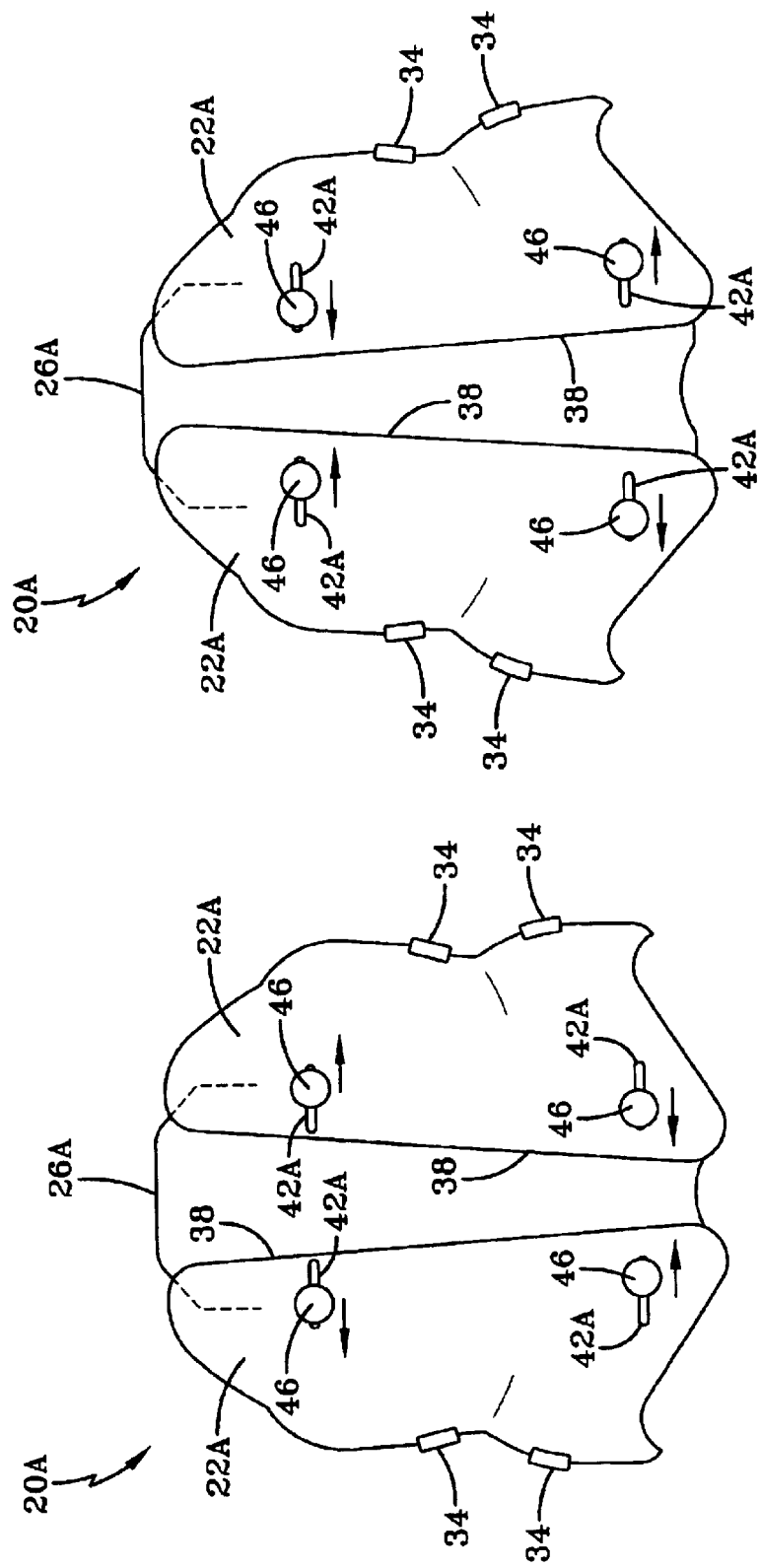

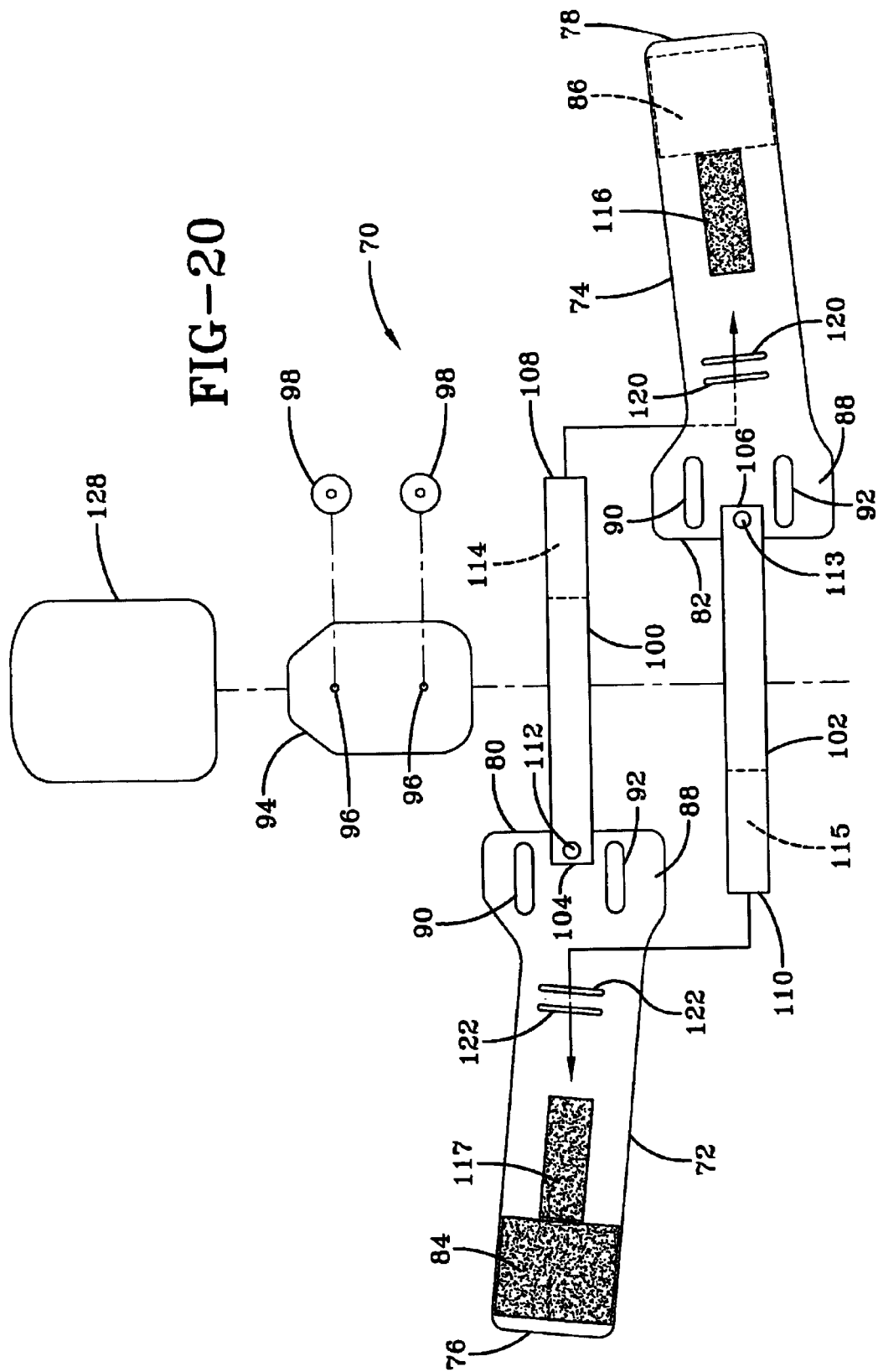

ORTHOSIS FOR SUPPORTING SPINAL STRUCTURES

CROSS-REFERENCES TO RELATED APPLICATIONS

This application is a continuation-in-part of U.S. pat. application Ser. No. 10/353,686 filed Jan. 29, 2003 now U.S. Pat. Ser. No. 6,840,916.

STATEMENT REGARDING FEDERALLY-SPONSORED RESEARCH AND DEVELOPMENT (Not Applicable)

REFERENCE TO AN APPENDIX (Not Applicable)

BACKGROUND OF THE INVENTION

1. Field of the Invention

This invention relates generally to orthotic devices generally and particularly to spinal orthotic devices useful to support the spine to provide varying degrees of immobilization of portions of the torso or trunk of the wearer.

2. Description of the Related Art

A common method of alleviating pain and promoting healing after an injury or spinal surgery is to provide stabilization of the patient's trunk and provide support for the involved spinal structural tissues. This is accomplished using a back brace or spinal orthosis. The terms brace and orthosis are used interchangeably herein.

There are a variety of spinal orthosis presently available, each possessing features which achieve varying degrees of support functions regarding the spine or related soft tissues. Of those which are generally accepted as the most useful, each have one or more features related to comfort to the wearer, the ease of use, and cost which also vary in degree. In most instances, one or more of these features are compromised to enhance other features.

Generally, it is accepted that a custom-made spinal orthosis, which is literally formed from a cast of the torso of the intended wearer, is believed to provide the highest degree of stabilization and support. However, custom made devices of this type possess drawbacks related to comfort, expense and the lack of adjustability should the dimensions or other circumstances of the wearer change during the time period required to wear the custom made device.

Highly adjustable devices, which may include elastic components of support, are advantageous relative to fitting a wide size range of persons and may offer some cost advantages. However, many of these devices offer a lesser degree of stabilization and support than desired.

There is also a class or type of spinal brace devices which are known as custom-fit. Such devices include pre-manufactured components which allow for some degree of latitude for fitting a given torso size and configuration. These devices may include adjustable features to achieve a better fit for the individual wearer. However, many of such custom-fit spinal orthosis rely upon flexible, non-rigid portions to achieve a certain degree adjustability or of comfort which may compromise the desired degree of immobilization and support of the wearer's trunk. Others of the custom fit type tend to be relatively limited in adjustment upon fitting and therefore require a greater number of standardized pre-fabricated components in order to accommodate a reasonable percentage of sizes and torso configurations typically encountered in the patient population.

There is a need for an improved custom-fit spinal orthosis of the type described which provides a satisfactory degree of comfort, manufacturing economy, and ease of proper fitting to the wearer, while also providing anterior, posterior, lateral and rotary control of the trunk equivalent to or closely approaching the same degree of immobilization of spinal structures achievable using the custom-made type torso cast.

There is also a need for an improved spinal orthosis which provides anterior and posterior control of the trunk which can be worn by many users suffering from general back pain from time to time due to overuse or less serious back strains which does not require fitting by a trained specialist, yet offers excellent support and adaptability to a wide range of torso sizes.

BRIEF SUMMARY OF THE INVENTION

The present invention relates to a spinal orthosis or back brace which is custom-fit to the individual wearer. The invention comprises a pair of rigid, or at least semi-rigid, arcuate side panels. The side panels, when mounted in opposing relationship, form a generally cylindrical configuration surrounding at least most of the torso of the wearer. Also included is a rigid or semi-rigid discrete posterior panel. The posterior panel is heat-deformable so as to be readily custom-fit to the lumbar curve of the wearer and is disposed under the side panels directly over a selected length of the wearer's spine.

A rear portion of the arcuate side panels extend in overlying relationship to the wearer's back and the posterior panel. The side and posterior panels include openings aligned with one another to receive a fastener to fix the side and posterior panels to one another. The openings allow lateral adjustment of the upper and lower portions of the side panels relative to one another which permits the orthosis to fit a wider range of different torso proportions within a given selected size range. This feature permits more economical volume manufacture of a smaller number of standardized components to efficiently and effectively meet custom-fit requirements accommodating a wide range of torso configurations.

Another preferred embodiment of the present invention relates to a spinal orthosis or back brace which does not require a custom-fit, yet provides a high degree of anterior and posterior support of the spine and related soft tissues. This embodiment employs discrete right and left side belt-like segments of flexible, non-elastic material which are configured to wrap around the wearer's torso in opposing directions and preferably overlap one another in the front and back of the wearer. A rigid or semi-rigid posterior panel similar to the panel described above is disposed under the posterior overlapping portions of the side segments. The posterior panel includes vertically spaced openings which are aligned with vertically spaced slots provided near the posterior edge of the side segments which are mutually connected by a fastener extended through the horizontal slots in the segments and aligned openings in the panel.

A strap is connected near the posterior edge of each side segment and extend circumferentially in opposing directions. Upon initially releasably attaching the overlapping front portions of the right and left side segments to one another, the opposing straps may be extended to tighten the side segments and releasably be fixed to segments to augment the fit and support provided to the wearer's trunk in the lumbar and sacral area.

The construction of this embodiment provides relatively facile self-fitting of the orthosis by the wearer to provide comfort and a high degree of support such that it may be worn during routine daily work or recreational activities.

It is therefore one aspect of the present invention to provide a spinal orthosis or brace which provides a high degree of stabilization and support for the targeted area of the spine.

It is another aspect of the present invention to provide an orthosis of the type described which is relatively easy to custom-fit to the selected wearer in an efficient and effective manner.

It is yet another aspect of the present invention to provide an orthosis of the type described which lends itself to economical manufacture of fewer standardized components to cover a wide range of body types and sizes and yet maintain the desired custom fit relationship with the individual wearer.

It is a further aspect of the present invention to provide a thoracic lumbar sacral orthosis (TLSO) or a lumbar sacral orthosis (LSO) which provides a high degree of comfort to the wearer which encourages patient usage of the device over the prescribed period of healing.

It is yet another aspect of the present invention to provide a TLSO or LSO which provides a rigid or semi-rigid shell-like configuration surrounding substantially the entire circumference of the wearer's torso to provide anterior, posterior, lateral and rotary control. This provides more positive stabilization of the wearer's trunk to promote the desired post-surgical or post-injury healing.

It is a further aspect of the present invention to provide a spinal orthosis which the user may self-fit without aid of a trained technician, and yet provides a high degree of adjustable, non-elastic lumbar-sacral support for easing general low back pain and stress.

Other aspects and objects of the present invention will become apparent from the following description.

BRIEF DESCRIPTION OF THE SEVERAL VIEWS OF THE DRAWINGS

FIG. 2 is a front elevational view illustrating an embodiment of the present invention in its intended operative position upon the torso of a wearer;

FIG. 3 is a rear elevational view illustration of the embodiment shown in FIG. 1 without showing the image of the torso of the wearer;

FIG. 6 is a rear elevational view of another embodiment of the present invention illustrating an modified posterior fastening arrangement for connecting the arcuate side panels to the posterior panel compared to that shown in FIGS. 3 and 5;

FIG. 7 is a rear elevational view similar to the view shown in FIG. 6 illustrating adjusting the rear panels relative to one another in a lateral direction opposite to that shown in FIG. 6;

FIG. 20 is a plan view of the components comprising another preferred embodiment of the present invention shown in exploded relationship illustrating a spinal orthosis of the non-custom fit type;

Figure 1:
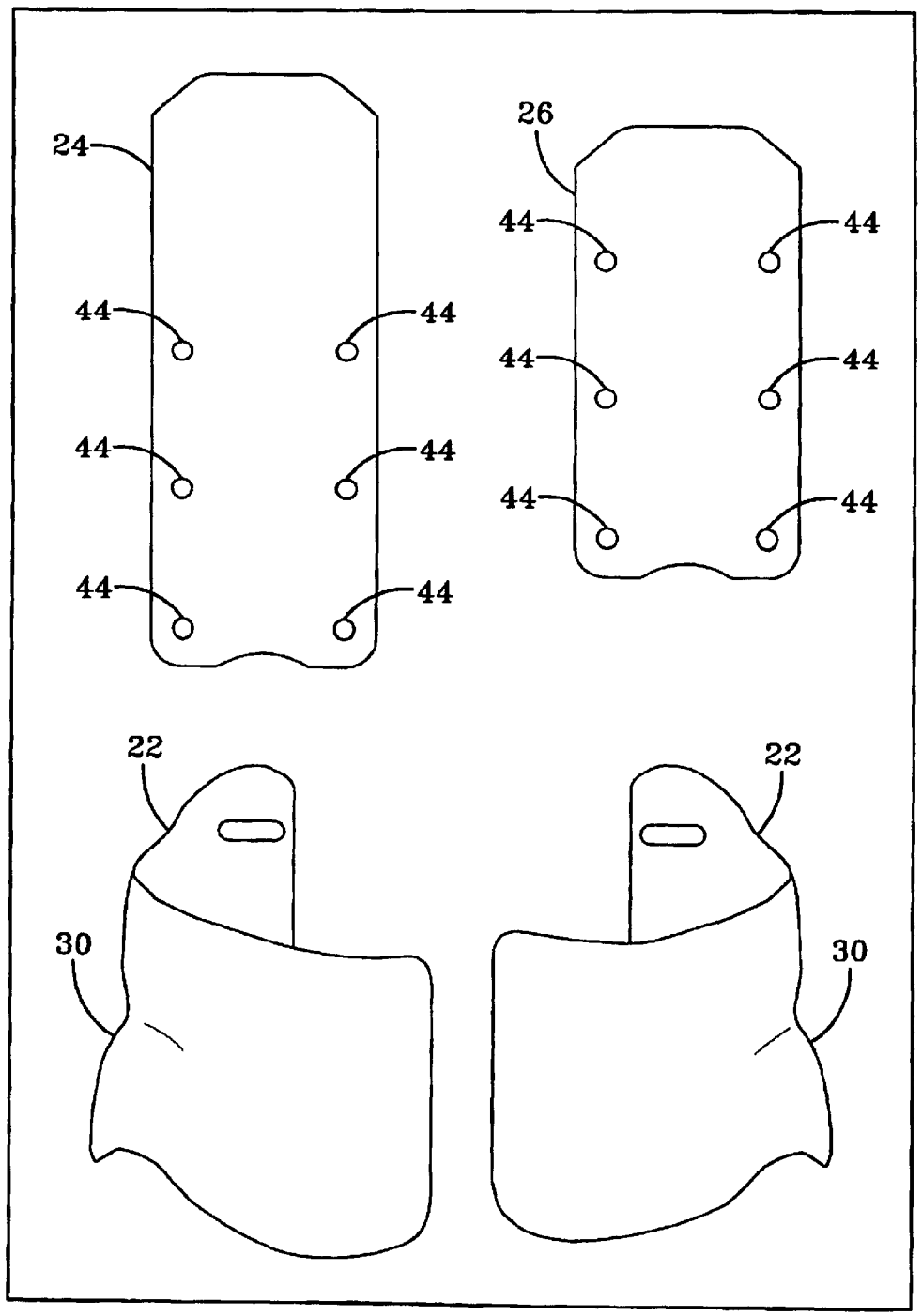
FIG. 1 is a perspective view showing individual components of an LSO spinal orthosis forming part of the present invention in exploded relationship.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art. In addition, components are illustrated which are of a type which perform well known functions. Those skilled in the art will recognize that there are many, and in the future may be additional, alternative arrangements which are recognized as equivalent because they provide the same function for the same purpose.

DETAILED DESCRIPTION OF THE INVENTION

A spinal brace or orthosis, indicated generally at 20, constructed in accordance with the present invention, is illustrated in FIGS. 1–3 and includes a pair of arcuate side panels 22 and one discrete posterior panel 24 or 26. The only difference between posterior panels 24 and 26 is the height dimension which is selected depending upon whether the orthosis 20 is designed to support only the lumbar sacral region, referred to by those in the art as an LSO type, or the thoracic lumbar sacral region, referred to as a TLSO. Otherwise, for purposes of the present invention, panels 24 and 26 are equivalent.

Side panels 22 and posterior panel 24 or 26 are preferably constructed from a heat-deformable or moldable semi-rigid or rigid material, preferably a suitable plastic. The terms semi-rigid or rigid, as used herein, mean that the panels may have some degree of flexibility, yet comprise an inelastic material having sufficient rigidity to provide a high degree of trunk immobilization when the components of orthosis 20 are operatively mounted on a wearer as described herein.

Side panels 22 are configured to conform to the torso of the wearer, such as seen in FIG. 2 when mounted on the wearer. The frontal portions of panels 22 surround the abdominal area from below the wearer's arm pits to the pelvic area. The front portion of an LSO brace should not extend lower than the pubic symphysis or higher than the xiphoid process just below the sternum. The rear portions of panels 22 extend between the lower end of the scapula over the back of the wearer to near the sacrococcygeal joint for an LSO design. In the LSO design, posterior panel 26 extends over the spine area generally about the same vertical length as the panels 22. For a TLSO design, the posterior panel 24 will extend up to the spine of the scapula and the front portions of panels 22 may also extend higher, if desired, to the upper end of the sternum.

Preferably panels 22 cover a portion of the upper hip area of the wearer. Each side panel 22 preferably includes a convex curve portion 30 adapted to accommodate the transition area on each side of the torso between the wearer's waist and hip.

For any given standardized size range, such as small, medium or large for example, frontal edges 32 of each panel 22 are adapted to overlap a portion of the opposing panel 22 so as to provide a closed configuration over the abdominal area of the wearer.

One or more pairs of flexible straps, such as 34, may be employed to function as a means to pull side panels 22 toward one another and into a releasably fastened, close fit relationship with the wearer's torso. One end of strap 34 may be fixed to one of the panels 22 with its free end aligned to extend horizontally across to the opposing panel 22. One preferred form of fixing strap 34 to the opposing panel 22 may take the form of the well-known Velcro hook and loop type fastener strips on the outward facing surface of the opposing panel 22 and the inwardly facing surface of the extendable strap 34. However, other forms of equivalent connecting means may also be used to advantage, including, for example, snaps, buckles, clasps and the like.

Using one form of the hook and loop fastening construction as seen in FIG. 2, each free end of an opposing flexible strap 34 extends laterally across toward the opposing panel 22. The outer surface of each strap 34 includes a cooperating strip of the hook and loop type. A conventional double buckle 33 accepts the free end of each strap 34. Then each, strap 34 may be doubled over itself and fastened via the hook and loop structure upon itself to draw side panels 22 toward one another to the desired degree. One or more pairs of additional straps 34 may be similarly employed as deemed desirable to accomplish the intended purpose as described herein.

It should be noted that the lower anterior edge 36 of each panel 22 is preferably disposed near the upper end of the pubic synthesis to assure coverage of most of the abdominal area of the wearer. When properly closely fitted on the wearer in accordance with the present invention and fixing of straps 34, the brace 22 provides a desirable increase in internal abdominal pressure. This increase in internal pressure in the abdominal cavity provides additional support to the spinal structures and the soft tissues supporting the spine.

Figure 5:
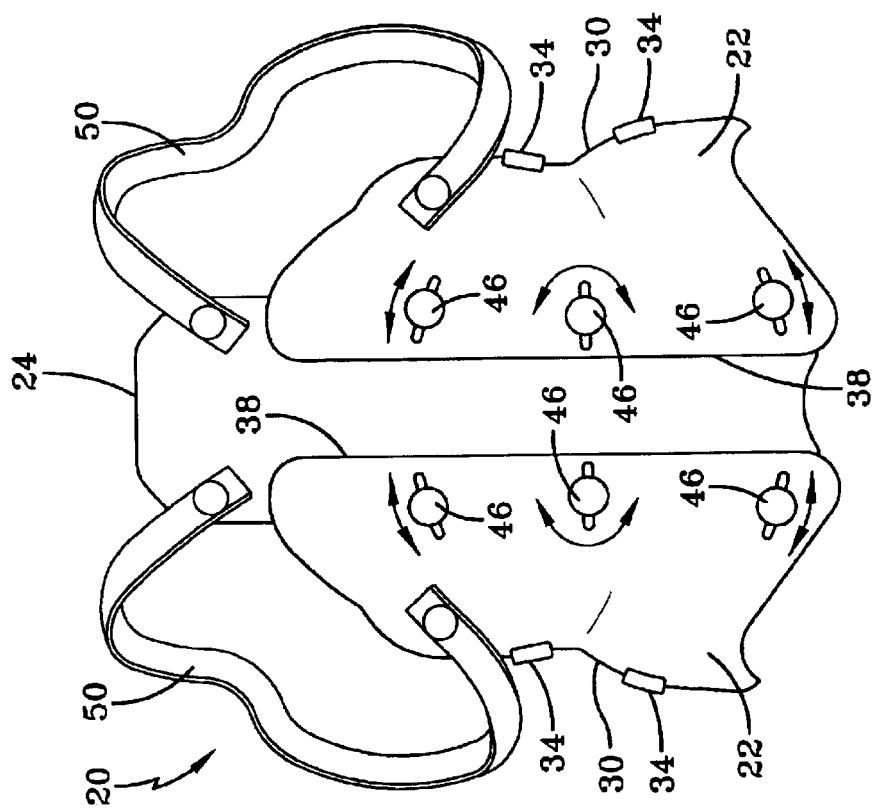
FIG. 5 is a rear elevational view similar to FIG. 3 showing the embodiment of the present invention illustrated in FIG. 4.

Each arcuate side panel 22 includes a rear portion extending across the back of the wearer's torso and may terminate in opposing posterior edges 38 located near the spinal area of the wearer, as shown in the embodiments seen in FIGS. 3 and 5.

The discrete posterior panel 24 or 26 is disposed under the rear portions of each side panel 22 over the wearer's back and aligned with the wearer's spine.

Panels 24 or 26 are preferably made of a semi-rigid or rigid, heat deformable plastic material. This allows essentially a pre-fabricated strip of planar material having preselected dimensions, to be heated and bent into a longitudinally curved configuration closely conforming to the measured anatomical curve of the lumbar vertebrae of the wearer. For convenience, the pre-fabricated strips may include a 25 degree curvature in the lumbar area which is typically within plus or minus a few degrees of the lumbar curve in most patients. Any final bending and molding to custom fit the posterior panel to the individual patient's lumbar curve would involve a modification typically less than three or four degrees.

Many plastic materials suitable for posterior panels 24 or 26 and side panels 22 are well-known to those skilled in the art. For posterior panels 22, those which soften sufficiently to allow relatively easy bending and molding into the required curved shape upon moderate heating and regain the original rigidity upon subsequent cooling are preferred. One preferred material is a polypropylene having a thickness in the preferred range of about 0.1 to 0.15 inches, and more preferably between about 0.12 to 0.13 inches. This range of thickness provides a panel of ample rigidity after being bent or molded into the final curved shape, is relatively inexpensive and is relatively lightweight for the comfort of the wearer.

The preferred thickness for side panels 22 is in the range of about 0.4 to 0.7 inches dependent upon the type of plastic material used. The choice of plastic material should take into account strength, hardness, and of course cost. Using an acrylonitrite, butadiene, styrene plastic composition, commonly referred to as ABS, it has been found that a thickness of about 0.6 inches performs well to provide the rigid arcuate configuration desired and suitably meet the other desired characteristics mentioned above. However, other materials in a range of thicknesses can be used to accomplish the desired results without departing from the present invention.

After heating and forming the posterior panel into the desired curved configuration fitting the patient's lumbar curve, cooling the panel to ambient temperature returns the panel 24 or 26 to its original semi-rigid or rigid condition. When positioned as described herein, the curved posterior panel closely fits over the spinal area of the wearer to provide, in combination with side panels 22, the stabilizing support intended when the brace 20 is appropriately fitted and fastened upon the wearer.

A plurality of vertically spaced slots, such as at 42, are provided adjacent to posterior edges 38 of each panel 22. Each slot 42 of one panel 22 is aligned in opposing, laterally spaced relationship to a similar slot 42 in the opposing panel 22 as seen in FIGS. 3 and 5.

In a cooperative manner, panels 24 and 26 are provided with vertically spaced openings 44 shown in the form of circular holes. Opposing ones of such holes 44 in a respective panel 24 or 26 are disposed for alignment with horizontally extending slots 42 in panels 22 when panel 24 or 26 is disposed beneath the rear portion of panels 22. Preferably, a threaded fastener, such as at 46, provided with a relatively large washer or an equivalent structure may be usefully employed to fix panel 24 or 26 to side panels 20 so as to more widely disperse the force or pressure applied by the fastener against the user's back.

A preferred fastener 46 of the Chicago type, shown in detail in FIGS. 16–19, includes a male threaded post 47 provided with an enlarged head 49. Post 47 mates within a tubular post 51, provided with internal female threads which is integrally formed with an enlarged back plate 53.

The enlarged head 49 and back plate 53 tend to disperse the pressure or force applied to the wearer's back when fastener 46 extends through holes 44 and slots 42 and is tightened to snugly fix the posterior and side panels to one another. The inner facing surfaces 55 and 57 may include an irregular or a roughened pattern to increase frictional engagement with the underlying surfaces of the panels upon final tightening of the fastener.

It should be pointed out the position of fasteners 46 within slots 42 determine the relative position of panels 22 to one another. Moving panels 22 proportionately toward or away from one another expands or contracts the generally cylindrical volume encompassed by brace 20. Movement of the upper or lower portions of each panel toward or away from the opposing panel provide for adjusting the interior volume of the upper and lower torso portions relative to a selected size and configuration standard. Therefore, persons having a larger or smaller upper torso configuration relative to their lower torso, compared to a selected average torso configuration, may be more readily accommodated to the desired custom fit within a given standardized size range.

This feature is important to provide an improved custom-fit device, yet minimize the number of standardized size ranges of pre-fabricated side panels 22 necessary to service the largest percentage of potential wearers. It should be noted that such an adjustment feature is accomplished using rigid or semi-rigid components which ultimately form a substantially rigid, close-fit cylindrical configuration surrounding the wearer's torso. This substantially rigid configuration provides a degree of stabilization and trunk support substantially equivalent to that achievable with a custom-made orthosis.

Figure 4:
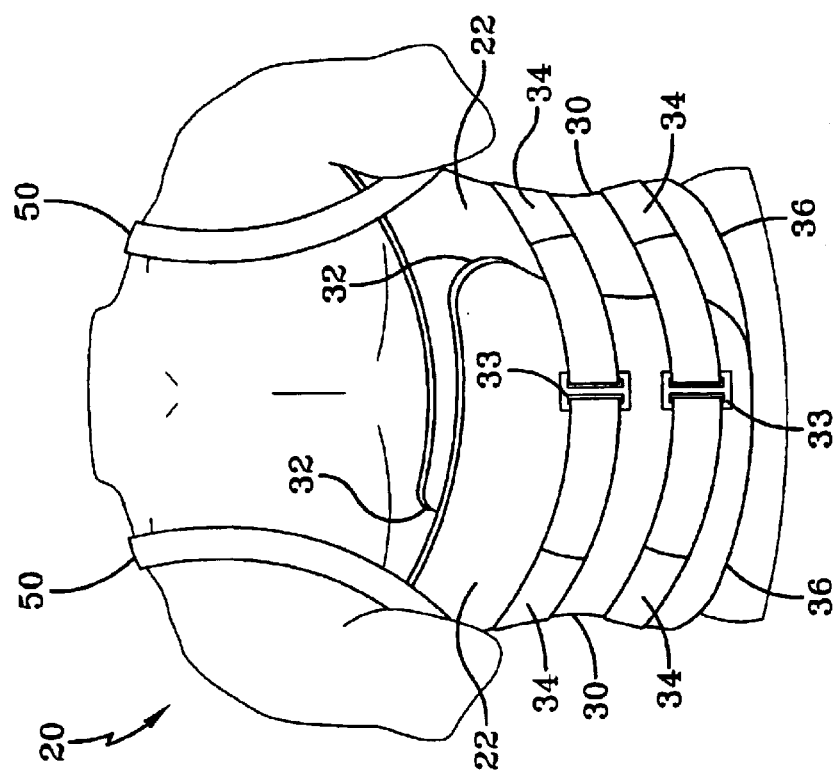
FIG. 4 is a front elevational view similar to FIG. 2 illustrating another embodiment of the present invention.
Figure 8:
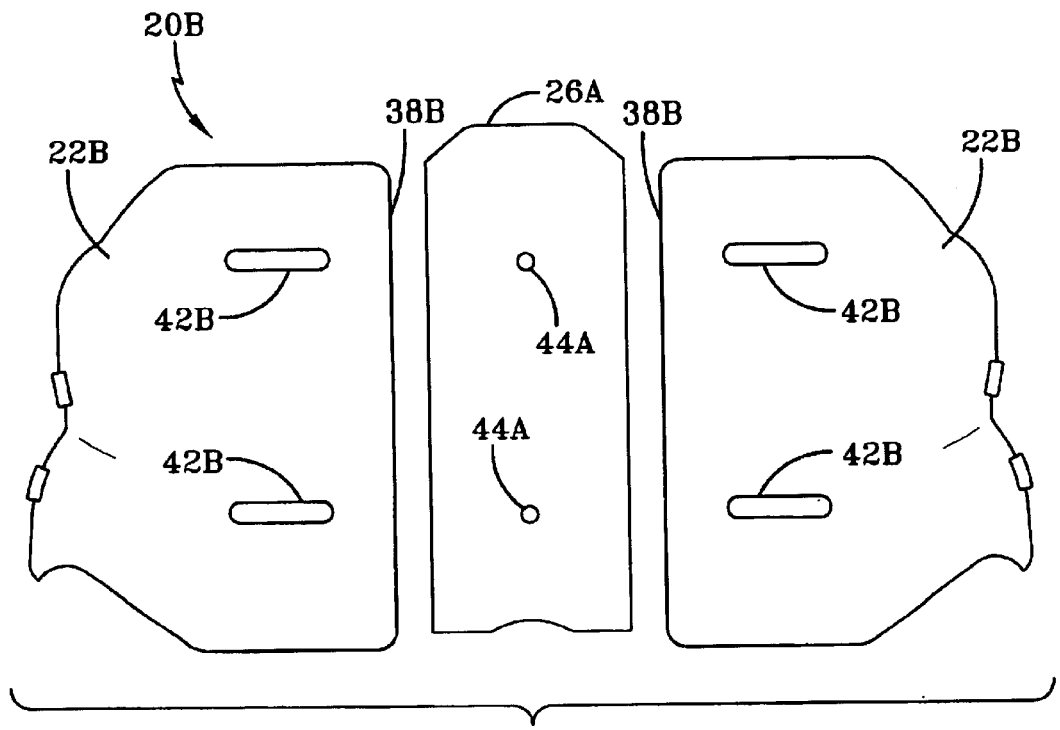
FIG. 8 is a rear elevational view of another embodiment of the present invention showing another modified arrangement for connecting the side panels to the posterior panel illustrating the components ion exploded relationship to one another.

With specific reference to FIGS. 4 and 5, the TLSO embodiment of the present invention using posterior panel 24 is shown which provides thoracic as well as lumbar sacral support. The difference between the embodiment shown in FIGS. 2 and 3 and that shown in FIGS. 4 and 5 relate only to the use of the longer posterior panel 24 instead of the shorter panel 26 and the provision of a pair of inelastic, flexible shoulder straps 50. Straps 50 extend over the shoulders and under the arm pits of the wearer to cooperate with the other components of brace 20 to reduce the mobility of the upper spinal column of the wearer. Each shoulder strap 50 is fixed at one end to panel 24 and at the opposing end to a respective one of side panels 22 as seen in FIGS. 4 and 5. The length of straps 50 may be made adjustable to fit snugly to the wearer in any suitable well-known and conventional manner as will be understood by one of ordinary skill. Upon tightening straps 50, the upper portion of brace 20 is stiffened to provide the intended support to the thoracic area and related spinal structures.

The remaining components of the embodiment shown in FIGS. 4 and 5 are the same as in the earlier described embodiment and carry the same reference numerals as the corresponding components shown in FIGS. 2 and 3.

Another preferred embodiment of the present invention is shown in FIGS. 6 and 7 which differs from the earlier described embodiments relative to the number of slots and holes provided in the posterior panel 24-A and the side panels 22-A. As seen in FIGS. 6 and 7, only two pairs of slots 42-A and aligned holes 44-A are required in posterior panel 26-A to accomplish the equivalent function as previously described regarding slots 42 and holes 44.

As shown in FIGS. 6 and 7, upon positioning of fasteners 46 at selected positions along slots 42-A while maintaining a selected fixed position of holes 44-A in posterior panel 24-A, the position of the upper portion of each panel 22-A relative to its lower portion may be adjusted to expand or contract the relative interior volume of the upper and lower portions of side panels 22-A. In a similar manner as previously described, this adjustment feature accommodates an improved close fit to particular anatomical contours of a wearer's torso, which deviate from a selected standard contour.

As best illustrated in FIGS. 6 and 7, it is evident that the posterior edges 38 of opposing panels 22-A can be tilted toward and away from one another to modify the proportional relationship between the upper torso area and the lower torso area engaged by brace 20. Within a selected size range, a given anatomical proportional contour of the torso may be selected as an average and used as a standard. Based upon such a standard, the dimensions and contour of the side panels 22-A may be selected such that the fixed positioning of fasteners 46 at approximately the midpoint of slots 42 or 42-A in the described embodiments would define the selected standard torso configuration relative to the proportions of the upper and lower trunk area of a wearer. This standard may be adjusted, as described, by positioning the fasteners 42 or 42-A toward either end of slot 42 or 42-A. This accommodates variations from the selected standard for a greater percentage of torso types otherwise generally within a selected size range.

In a similar manner, posterior panels 24, 24-A and 26, 26-A may be prefabricated using a set of standardized lengths to accommodate any significant difference in the length dimension necessary to extend over the necessary portion of the wearer's spine to provide the intended immobilization and support of the wearer's trunk. Typically, however, it has been found there is not a great difference in length necessary to accommodate differences in the height of most persons for the LSO or TLSO type brace.

It should also be noted that the spinal orthosis of the present invention may include a conventional interior lining comprising a pad of resilient material, preferably a foamed plastic, not shown. The pad provides an additional degree of comfort to the wearer. Such a pad lining preferably may be releasably fixed to the interior walls of panels 22 in any conventional manner well-known to those of ordinary skill in the art. A separate pad liner may also be releasably fixed to the inner facing surface of posterior panels 24 or 26.

Now referring to FIGS. 8–11, another preferred embodiment of the present invention is illustrated. The basic difference between the embodiment shown in FIGS. 8–11 relative to that shown in FIGS. 6 and 7 is that the posterior edges 38-B of panels 22-B are extended such that the edges 38-B overlap portions of the opposing side panel 22-B. Modified components or parts of this embodiment relative to the corresponding embodiments shown in the preceding Figs. are indicated by the same reference numeral followed by the letter "B".

One primary advantage of having overlapping posterior edges 38-B is that the number of slots 42-B, holes 44-B and fasteners 46-B may be reduced and yet provide an equivalent connecting function compared to those previously described in relation to the other embodiments. This overlapping feature of the rear portion of panel 22 is advantageous as it tends to simplify and reduce the time necessary for the custom-fitting procedure as compared to the embodiments shown in the preceding Figures.

Figure 9:
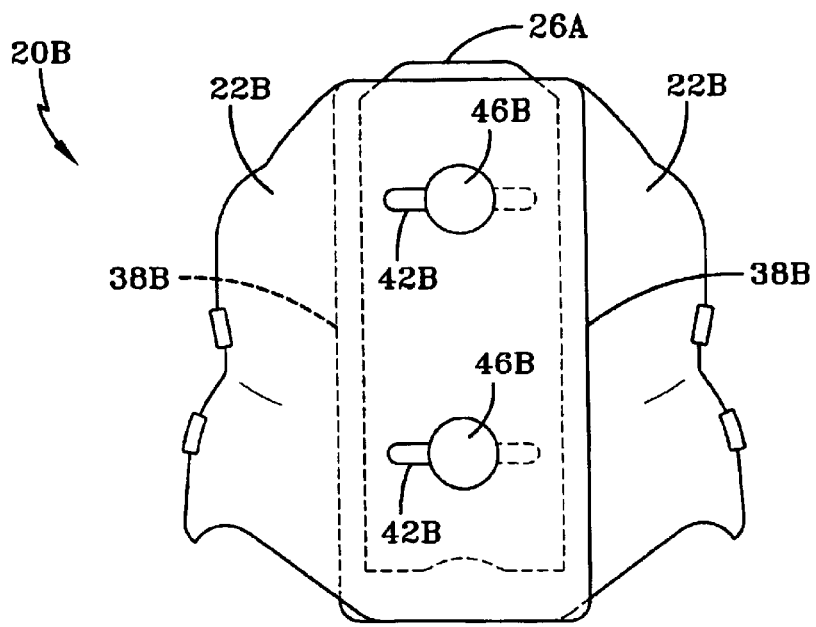
FIG. 9 is a rear elevational view of the embodiment shown in FIG. 8 illustrating the component panels connected to one another as if they were mounted on a wearer.

As best seen in FIG. 9, the spinal brace 20-B is shown in assembled form with the opposing edges 38-B of the side panel 22-B on the left, overlying a portion of the side panel 22-B seen on the right. The embodiment shown in FIGS. 8–11 tends to permit the practical length of slots 42-B to be increased compared to the earlier described embodiments without sacrificing structural integrity or fit. The greater the length of slot 42-B, the greater degree of adjustability may be attained.

It should also be noted that the disposition of slots corresponding to 42 and openings or holes corresponding to 44 may also be reversed between the panels 22 and posterior panels 24 or 26 without departing from the present invention. However, placing the slots in the side panels and the holes in the posterior panel as shown is believed to be more preferred.

The custom-fitting of brace 20 to the wearer should be done by properly trained personnel and is essentially the same for all embodiments. Side panels 22 are held in surrounding relationship to the torso and slots 42 are aligned with the openings 44 in the underlying posterior panel 26 or 24.

Referring specifically to the embodiment shown in FIGS. 8–11, the fitting may be more quickly accomplished since only two fasteners 46-B are required. As seen in FIG. 9, the opposing posterior edges 38-B are aligned substantially parallel to one another and fasteners 46-B are disposed through approximately the middle of slots 42-B and into the underlying opening 44 in posterior panel 24-B and tightened lightly to connect the rear portions of panels 22-B to the posterior panel.

Figure 11:
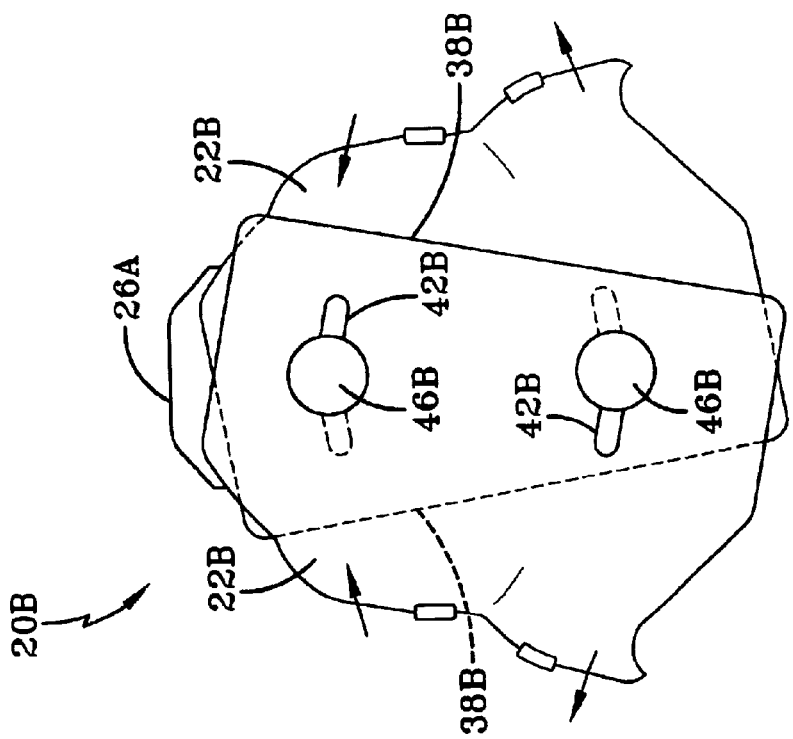
FIG. 11 is a rear elevational view of the embodiment shown in FIG. 9 illustrating the side panels laterally adjusted in an opposite position relative to that shown in FIG. 10.
Figure 10:
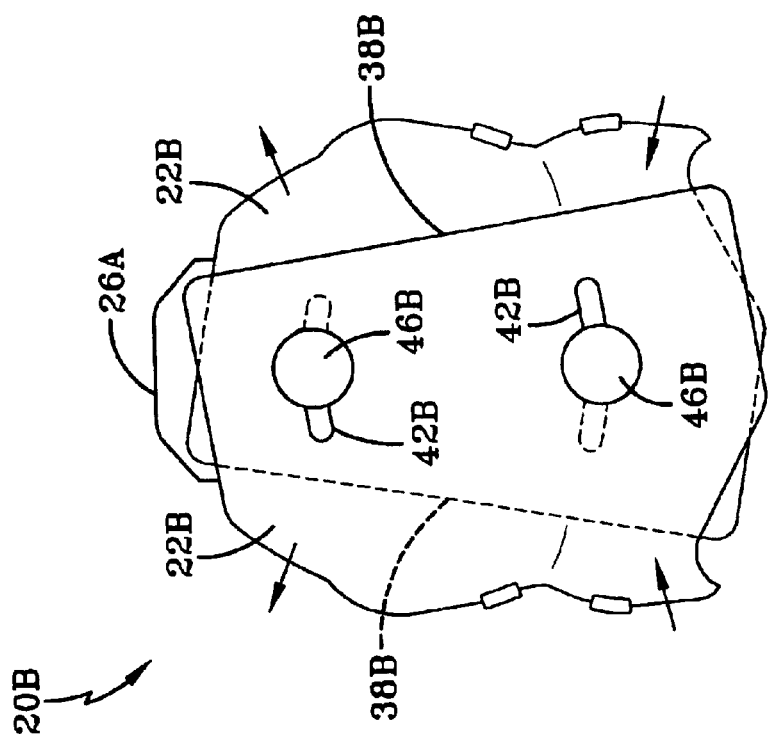
FIG. 10 is a rear elevational view similar to FIG. 9 illustrating the side panels laterally displaced compared to that illustrated in FIG. 9 to adjust the fit to a given wearer's torso proportions.
Figure 12:
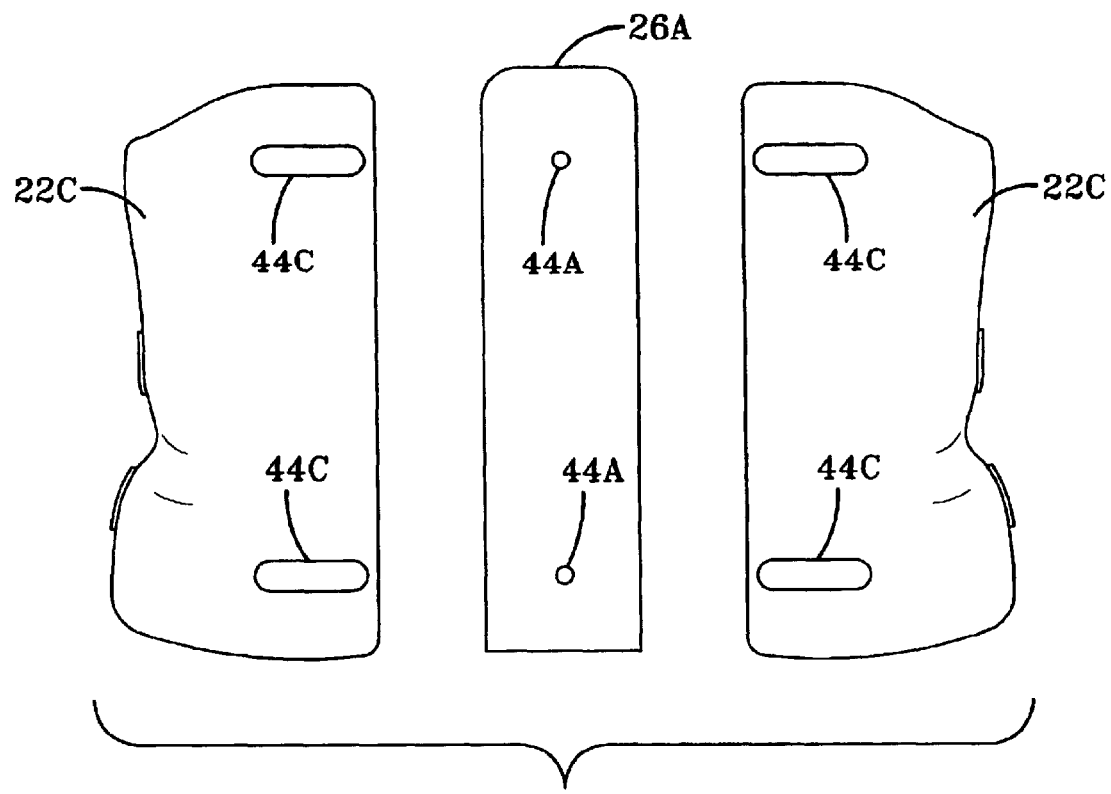
FIG. 12 is a rear elevational view of another embodiment of the present invention illustrating the components of a TLSO version of the orthosis in an exploded relationship.
Figure 13:
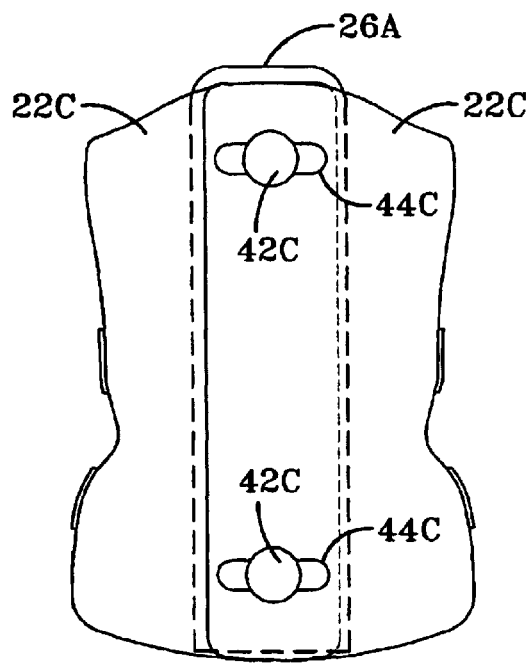
FIG. 13 is a rear elevational view of the embodiment shown in FIG. 12 illustrating the components panels connected to one another as if they were mounted on a wearer.
Figure 14:
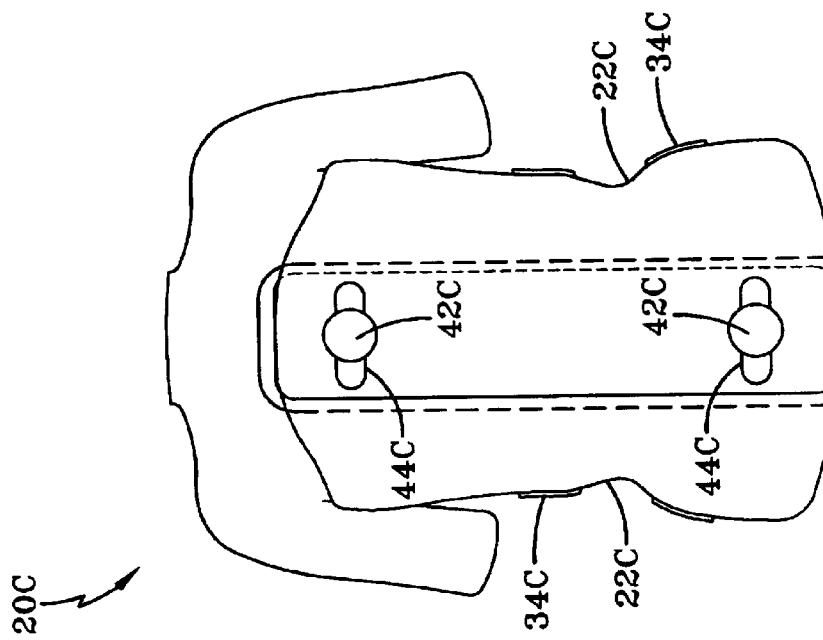
FIG. 14 is a front elevational view of the embodiment shown in FIG. 13 illustrating the embodiment mounted on a wearer's torso.
Figure 15:
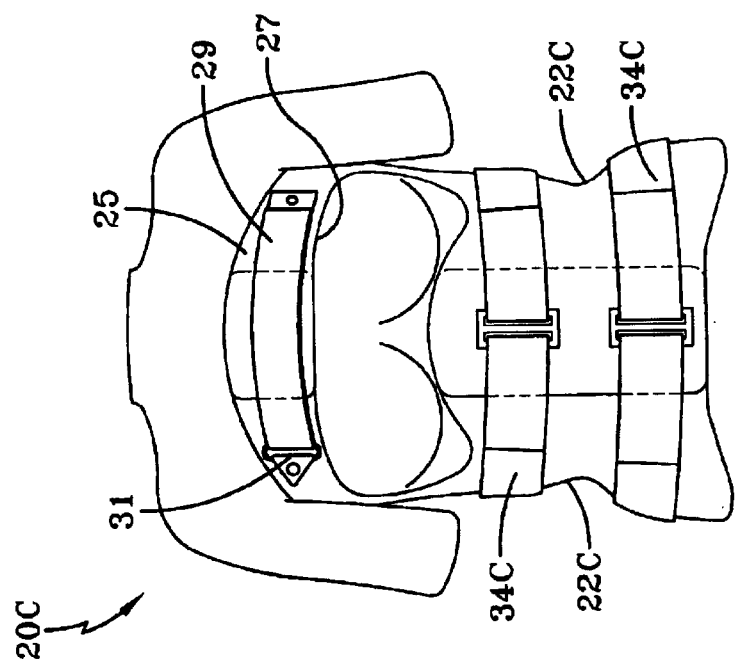
FIG. 15 is a rear elevational view of the embodiment shown in FIG. 13 illustrating the embodiment mounted on a wearer's torso.
Figure 18:
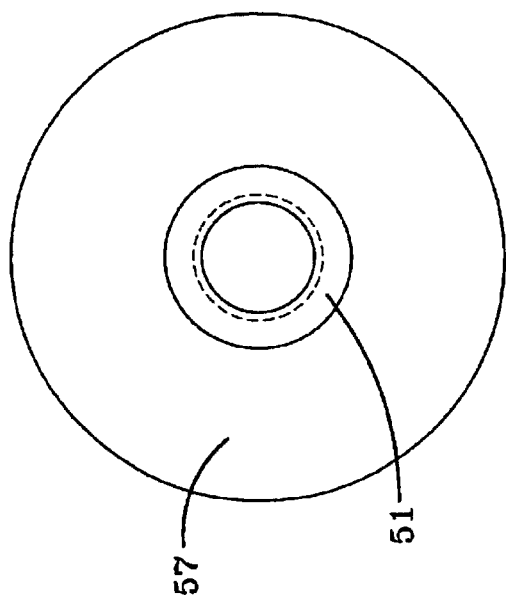
FIG. 18 is a bottom view of the female portion of a preferred fastener forming a part of a preferred embodiment of the present invention.
Figure 19:
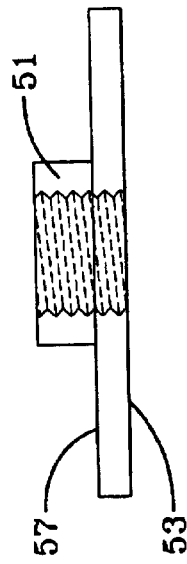
FIG. 19 is a side elevational view of the female portion shown in FIG. 18, the internal threaded bore being shown in section for clarity of illustration.
Figure 16:
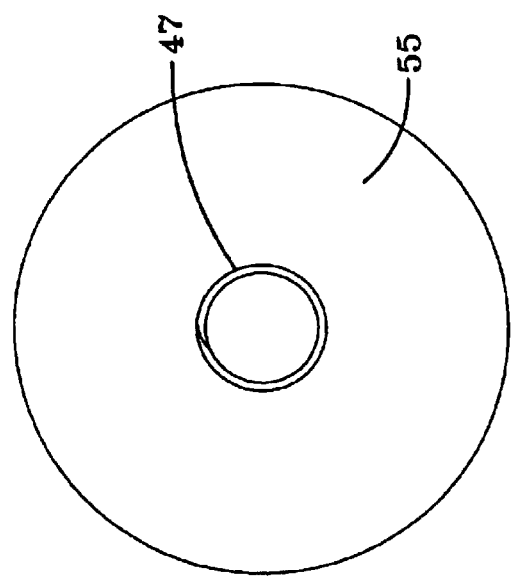
FIG. 16 is a bottom view of the male member portion of a preferred fastener forming a part of a preferred embodiment of the present invention.
Figure 17:
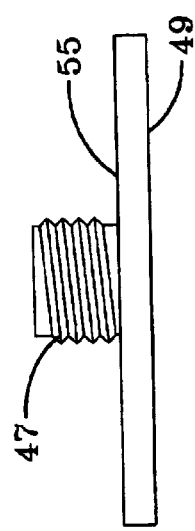
FIG. 17 is a side elevational view of the male member shown in FIG. 16.

FIGS. 10 and 11 illustrate the maximum adjustment in opposing directions employing the construction of the present invention relative to accommodating persons having larger or smaller upper and lower torso proportions relative to the proportions of a selected standard configuration which is represented by the arrangement shown in FIG. 9. As seen in FIG. 9, posterior edges 38 are aligned substantially parallel to one another.

As seen in FIG. 10, the circumference of the lower torso portion of the brace 20-B is reduced relative to the upper portion to accommodate a corresponding torso configuration of a wearer. This may be accomplished by moving the upper portion of side panels 22-B away from one another prior to final tightening of fasteners 46-B within slots 42-B and openings 44-B. This has the effect of pivoting the side panels about the holes 44-A in the posterior panel 26-A. In making this adjustment, the fasteners 44-B are disposed toward opposite ends of the upper and lower slots 42-B. Upon tightening fasteners 46-B in the conventional manner, the brace is releasably fixed in this modified disposition.

Adjustment of the lower portion of brace 20-B is accomplished in the reverse manner, as shown in FIG. 11, to expand the circumference of the lower torso portion of brace 20-B relative to that shown in FIGS. 9 and 10. This has the effect of reducing the circumference of the upper portion of the brace 20 covering the upper torso.

Of course, the side panels 22-B may also be equally moved toward and away from one another to dispose fasteners 46-B at the left or right end of upper and lower slots 42-B. In this manner, the general contour shown in FIG. 9 is maintained, however, the circumference of the upper and lower portions of brace 24 has been expanded or contracted equally to accommodate the torso of the wearer.

The fasteners 46 in any of the embodiments are typically positioned as described and initially tightened lightly to connect panels 22 together in the rear and may be subsequently tightened once the intended fitting adjustments have been made.

Next, the frontal edges 32 of panels 22 are urged together and strap 34 is fastened to strip 35 to hold the brace 20 in a general initially mounted position. The trained personnel then begin to make any further adjustments in the positioning of fasteners 46 deemed needed and adjust the strap or straps 34 accordingly until a proper fit is accomplished. Simply loosening the head of a fastener 46 allows further adjustment, followed by tightening the fastener until the desired fit and comfort level has been achieved.

Now referring to FIGS. 12–16, another embodiment of the present invention is shown. Components of this embodiment are identified by the same reference numeral used for a corresponding component followed by the letter "C". The primary difference of the embodiment of FIGS. 12–15 relates to a modification of the frontal portion of the side panels to include an upper portion located above the breast line of the wearer. This construction provides a TLSO orthosis which does not require the straps 50 such as shown in the embodiment illustrated in FIGS. 4 and 5.

Referring to FIGS. 12–15, side panels 22-C include slots 44-C and extend over the spine of a wearer to a height greater than the LSO version shown in the preceding Figures such as FIG. 3. Additionally, the panels 22-C include an upper portion 25 which overlaps the corresponding portion 25 of the opposing panel and extends across the wearer's chest above a cut-out portion 27 aligned with the breast of the wearer. An additional strap 29 is fixedly provided on one panel 22-C which, in cooperation with a buckle 31 fixed on the opposing panel and velcro-like strips, function to tighten and hold the upper portion of panels 22-C in close-fitting relationship in a similar fashion to straps 34-C which draw the lower torso portion of brace 20-C together.

The added upper portion 25 of each side panel 22-C function to inhibit forward bending in the thoracic spine. Upon properly mounting brace 20-C, upper portion 25 is effectively connected to posterior panel 26-A as well as being an integral part of each side panel 22-C. This construction is preferred and replaces the need and function of straps 50 shown in FIG. 5.

The rearward facing portions of side panels 22-C are the same in all essential respects to the embodiment shown in FIGS. 12–15 regarding slots 44-C, fasteners 46-C and TLSO type posterior panel 26-A as previously described herein. This includes adjusting the relative proportions of the upper and lower torso portions comprising brace 20-C relative to a selected standard as described herein. The description of such adjustments being essentially identical to those described for the embodiment of FIGS. 12–15 will not be repeated since it is believed unnecessary for one of ordinary skill in the art to understand how to make and use the present invention and this embodiment.

In view of the foregoing description, it should be readily understood that the present invention provides a custom-fit type of LSO and TLSO type orthosis wherein prefabricated components may be manufactured in an economical manner to provide a degree of immobilization of the trunk of the wearer equal to or closely approaching the results obtained using a custom-made brace.

Further, a custom-fit LSO or TLSO constructed in accordance with the present invention provides a degree of comfort which tends to increase patient compliance for the prescribed time period during which the brace should be worn. The present invention also provides prefabricated components which may be readily custom-fit to the wearer in a relatively facile and quick manner compared to prior custom made spinal braces and yet provide a closely similar level of stabilization and spinal support more economically.

Now with reference to FIGS. 20–26, another preferred embodiment of the present invention is illustrated wherein a spinal orthosis, indicated generally at 70, which is of the non-custom fit type, comprises right and left side belt-like segments 72 and 74. Each side segment is discrete and comprise a non-elastic, flexible material. A plastic material is preferred for strength and economical manufacture.

The anterior edges 76, 78 of segments 72, 74 and their posterior edges 80, 82 define a preferred length dimension configured to permit each side segment to be wrapped in opposing relationship around a wearer's torso such that the respective anterior and posterior edges of each segment overlap those of the other segment as described below.

A releasable fastening means, preferably comprising complimentary patches of the well-known hook and loop fastening material, such as at 84 and 86, is provided near the anterior edges 76 and 78 over a surface portion of segments 72 and 74 to permit the segments to be releasably fastened to one another over the abdominal area of the wearer, such as shown in FIG. 2.

Each of the side segments 72, 74 includes a widened area 88 located near their respective posterior edges 80, 82. These widened areas 88 taper to a narrower width in a direction toward their anterior edges 76, 78. Each widened area 88 accommodate a pair of vertically spaced, horizontally extending slots 90 and 92 which are configured to at least partially overlie one another when the segments 72 and 74 are appropriately wrapped around the wearer's waist area.

A rigid or semi-rigid lumbar support panel 94, preferably similar to the panel 24 described earlier herein, is designed to fit over the lumbar-sacral area of the wearer's spine. The panel 94 is provided with a curvature, such as 25 degrees, so as to generally conform to the lumbar curve of the average lumbar curvature found in most individuals, which typically varies no more than a few degrees.

Posterior panel 94 is provided with at least two vertically spaced openings or holes 96, each disposed to align with a respective one of the slots 90 and 92 in a respective one of side segments 72, 74.

A fastener 98, which may be the Chicago type such as fastener 46 described earlier herein, or alternatively, the shaft of a conventional plastic rivet type fastener with an enlarged head, is operatively extended through the aligned slots 90 and 92 and the underlying aligned holes 96 and fixed in a conventional manner to adjustably connect the posterior portions of each segment 72, 74 to one another and to connect each segment to panel 94. It is preferred that each fastener 98, or an equivalent type rivet fastener, not be tightened to an extent that prevents relative slideable movement between fasteners 98 and slots 90 and 92 to allow adjustment of the effective length of side segments 72 and 74 relative to holes 96 in panel 94.

A pair of straps 100 and 102 are provided, each having a fixed end 104 and 106 respectively, and a free end 108 and 110. Fixed end 104 of strap 100 is connected via a rivet 112 or other suitable conventional fastening means, to widened area 88 of left segment 72 near posterior edge 80 with its free end 108 extended across panel 94 in a direction along the length of right segment 74 toward the anterior edge 78. A suitable patch of the hook and loop type fastening material 114 is attached to strap 100 near free end 108 and may be releasably attached to a complimentary patch of hook and loop material 116 disposed on an outwardly facing surface of right segment 74.

In an opposing, but similar manner, fixed end 106 of strap 102 is connected by a rivet like fastener 113 to widened area 102 of right side segment 74 with its free end 110 extendable across panel 94 and along the length of left side segment 72 to be releasably connected to left side segment 72 via hook and loop fastening patches 115 and 117, such as seen in FIG. 20 in a similar manner as described above.

Figure 24:
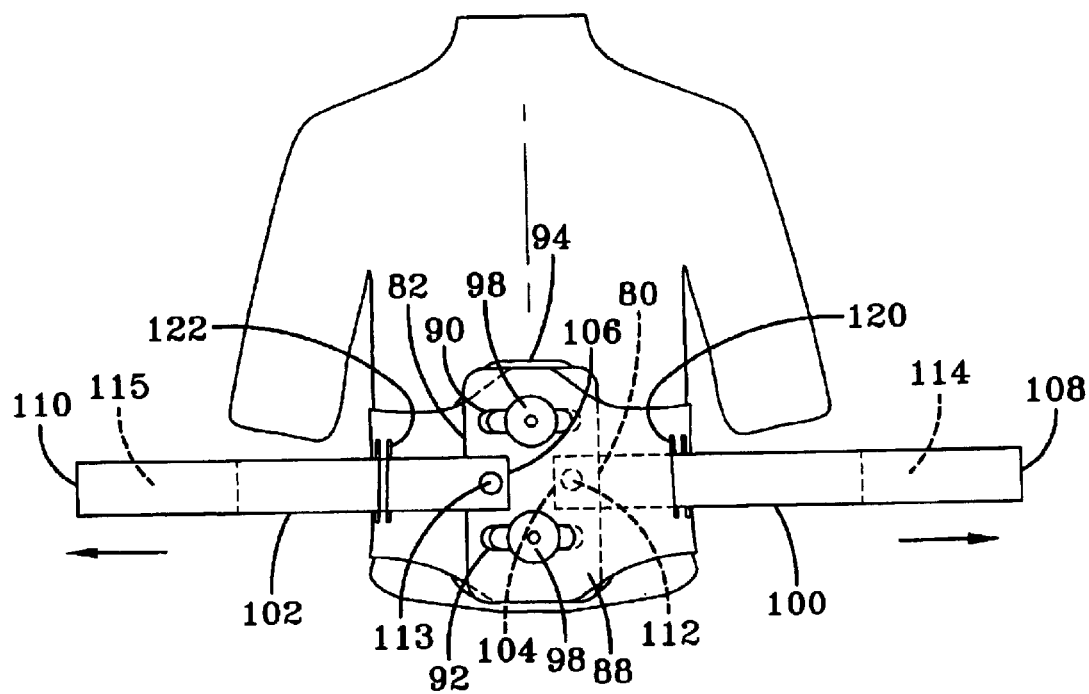
FIG. 24 is a rear view of the orthosis as shown in FIG. 23 illustrating the step of pulling the posterior straps forwardly to slideably adjust the effective circumference of the orthosis upon the wearer.
Figure 26:
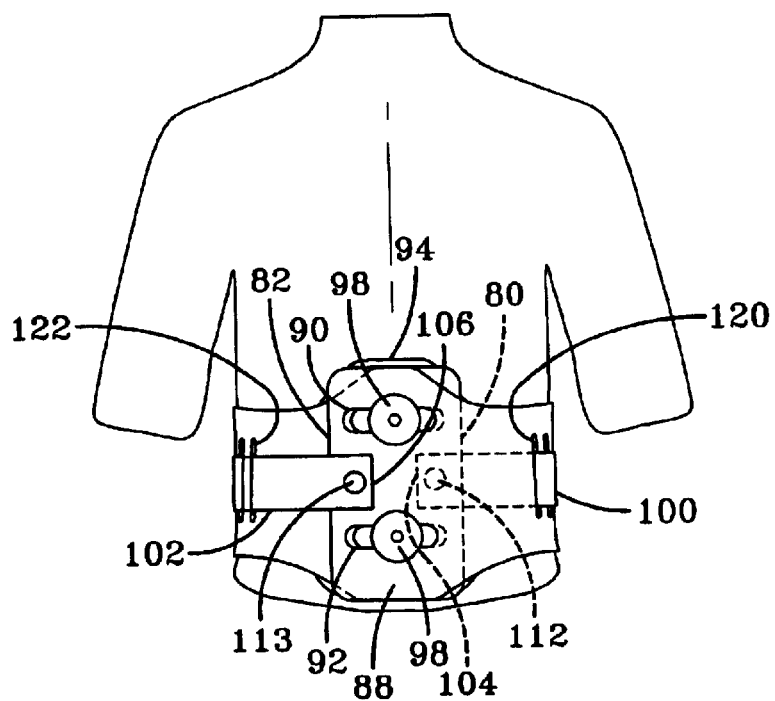

To better accommodate the overlapping posterior portions of segments 72 and 74, straps 100 and 102 upon being extended in opposite directions, pass through at least one of a pair of vertically extending slots or openings 120 and 122 which are provided in side segments 72 and 74. This allows strap 100, for example, to pass under the opposing segment 74 and then pass upwardly through one of slots 120 as shown in FIGS. 24 and 26, and then along the outer surface of segment 74 for attachment of patch 114 of strap 100 to patch 116 on segment 74.

The strap 100 threaded through one of the openings 120 enhances the ease of applying tension upon strap 100 for further tightening of the belt segment as described later herein. In a similar fashion the extension of strap 102 through each of slots 122 and immerge along the outer surface of segment 72 also aids in this manner.

It is desirable, but optional, to provide a liner of soft material, such as pad 128, to overlie the rear surface portion of panel 94 to provide additional comfort to the wearer. Liner pad 128 may comprise one of several conventional materials such as a fabric covered foam plastic or the like and be attachable to the inwardly facing surface of panel 94 using any well-known conventional means. Preferably, pad 128 may be releasably fixed by providing one or more areas of the conventional hook and loop fastening material to the confronting surfaces of pad 128 and panel 94 in any well-known conventional manner.

Figure 21:
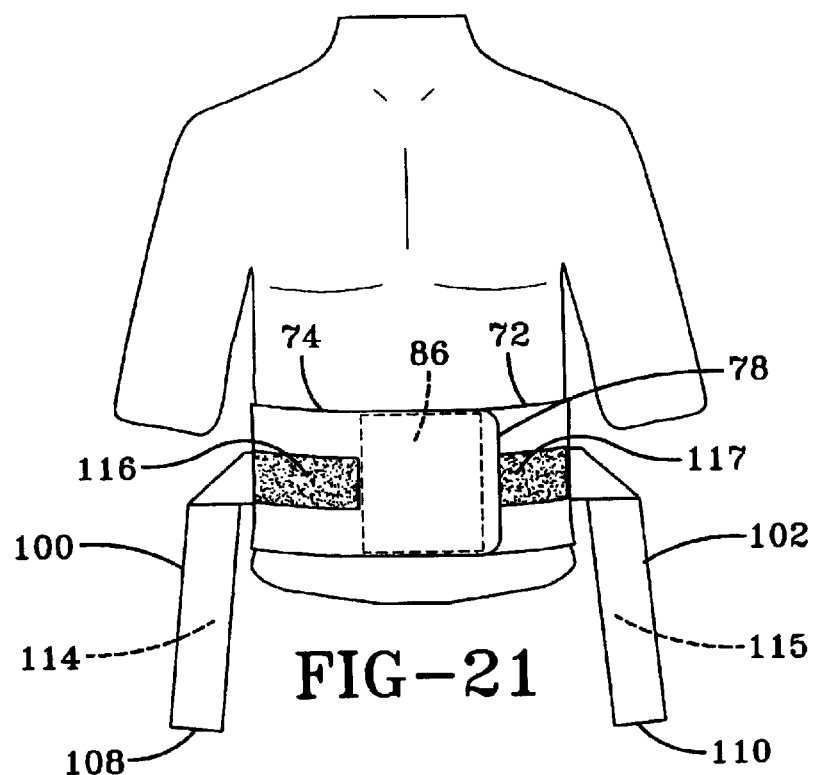
FIG. 21 is a front view of the orthosis shown in FIG. 20 assembled and initially positioned on the torso of a wearer.
Figure 22:
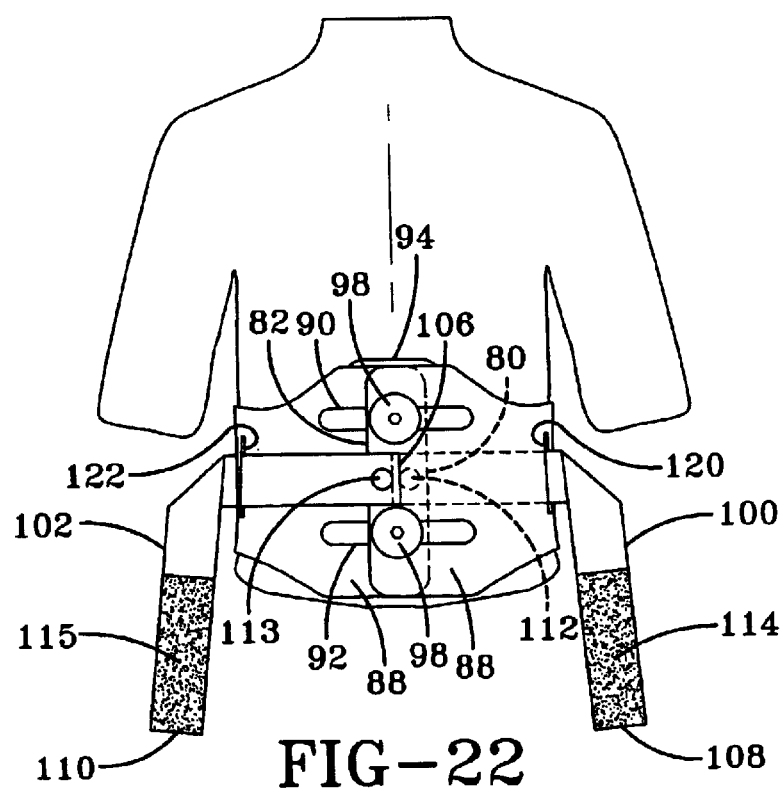
FIG. 22 is a rear view of the orthosis shown in FIG. 21 as initially positioned on the wearer.
Figure 23:
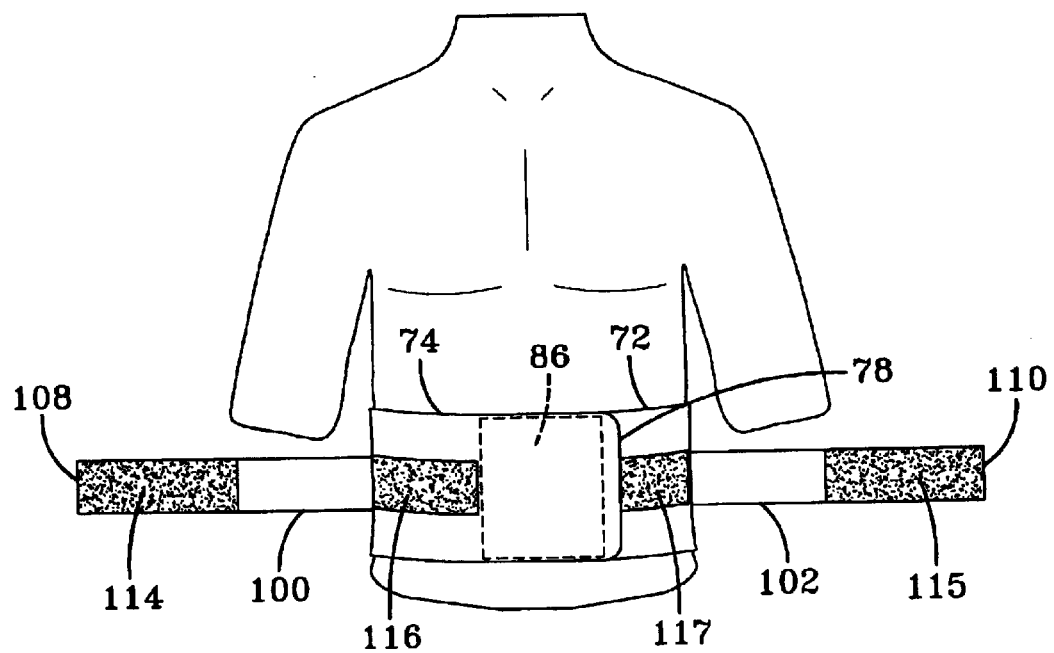
FIG. 23 is a front view of the orthosis shown in FIG. 21 illustrating the posterior straps in an extended position in the next step of properly positioning the orthosis on the wearer.

It should be noted herein that the fasteners 98 extended through slots 90 and 92 and openings 96 are preferably not tightened to a degree that prevents slidable, horizontal movement of segments 72 and 74 via sliding respective slots 90 and 92 relative to fasteners 98 upon wrapping the segments 72 and 74 around the wearer's waist and initially attaching the anterior portions of the segments via the overlap of fastening areas 84 and 86. This initial positioning and placement of the orthosis simply requires the wearer to pull the respective forward end of the segments toward one another to a relatively snug fit and fix the anterior portion of each segment to one another as earlier described herein such as shown in FIGS. 21 and 22, for example.

Figure 25:
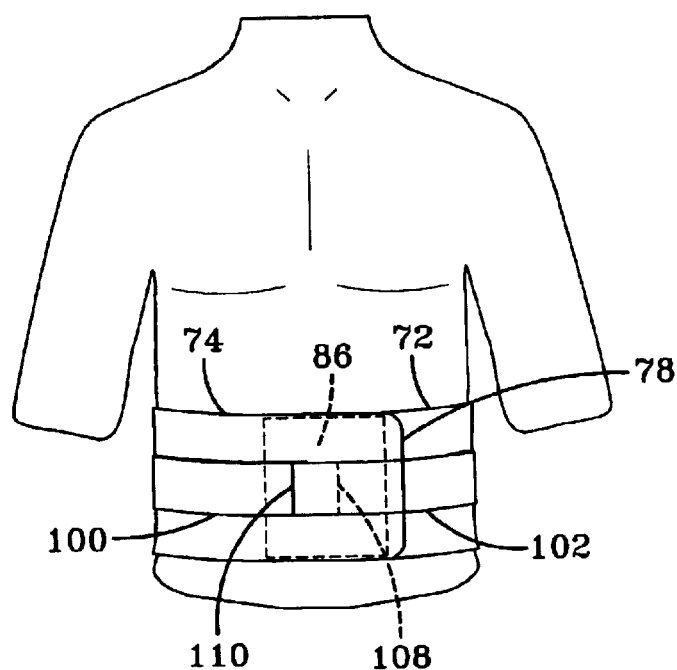
FIGS. 25 and 26 are front and rear views of the orthosis shown in the preceding FIGS. 20–24 fully mounted in its intended operative position upon the wearer.

However, to achieve maximum support and a tighter fit as indicated by the arrows in FIG. 24, the free ends 108 and 110 of straps 100 and 102 may be pulled in opposing directions and then fixed to the opposing side section at fastening areas 116 and 117 as seen in FIGS. 25 and 26. The tightening of straps 100 and 102 in this manner provides improved leverage to draw the side segments 72 and 74 more tightly around the wearer and particularly to provide increased compression in the posterior portion of the orthosis, including positioning the lumbar support panel 94 more firmly against the spinal area of the wearer. This tends to provide excellent support in a comfortable manner to the wearer. Further, upon fixing straps 100 and 102 in tension in this manner, the side segments 72 and 74 are effectively fixed relative to one another and slots 90 and 92 are no longer free to slide relative to fasteners 98 until straps 100 and 102 are released from areas 116 and 117 to release the tension in the straps.

This construction provides similar functionally equivalency to that obtained using an elastic material to automatically adjust the compression and fit of the orthosis to the wearer, but possess the additional advantage of permitting a non-elastic degree of support once the straps 100 and 102 are pulled into tension with their free ends fixed as described. Elastic materials are known to lose their elasticity upon frequent use over time. The construction of the present invention using inelastic materials does not exhibit this less desirable result yet maintains the beneficial feature of adjustable non-elastic support.

This secondary tightening via straps 100 and 102 also allows the wearer to very conveniently adjust the degree of compressive forces applied around the wearer's torso to correspond to the activity level being performed without removing the orthosis from its position around one's waist.

For example, should the wearer be involved in a work or recreational activity wherein extra support is desirable for the lumbar and sacral area, the free ends of straps 100 and 102 may be pulled forwardly to apply the maximum tension and fastened to achieve a tighter fit providing the greatest support. Such tightening increases the internal abdominal pressure as well as the pressure of posterior panel against the spinal area, as earlier described, both of which enhance support in the lumbar sacral area.

If the wearer desires to rest or assume a sitting position, but not remove the orthosis 70, one may merely loosens free ends 108 and 100 and re-attaches them with a lesser degree of tension to establish a lessened degree of compression.

When activity is resumed, a simple and facile manipulation to loosen the free ends of straps 100 and 203 and re-tighten them as described is all that is necessary to provide the fit and increased level of support desired.

As a further benefit, the adjustment of side segments 72 and 74, as described herein, allow a significant range of torso sizes to be accommodated with the same size orthosis and still achieve an excellent fit around a wearer's torso. This can be readily appreciated by noting the overall girth or effective circumference available to a wearer can be adjusted not only by the degree of overlapping attachment obtained in the front of the wearer via the horizontal dimensions of hook and loop patches 84 and 86, but also the overlapping range in the posterior portions provided along the length of horizontally extending slots 90 and 92.

The secondary tightening feature alone, provided by the construction described herein, allows the orthosis to be fixed in a supporting relationship spanning almost twice the length of slots 90 and 92. With slots 90 and 92 being merely 2 to 3 inches long, the available adjustment may conveniently span approximately 4 to 6 inches without creating any significant change in the manufacture, design and cost of the orthosis constructed in accordance with the present invention.

It is also pointed out that this wide range of girth or circumference adjustment permits an orthosis of the type described to be made in as few as three basic sizes which would effectively and comfortably fit essentially all but a few of the potential users of the orthosis constructed in accordance with the present invention. Of course, if deemed desirable, one could manufacture a petite and extra large size as may be necessary to cover substantially the non-average girths.

Figure 27:
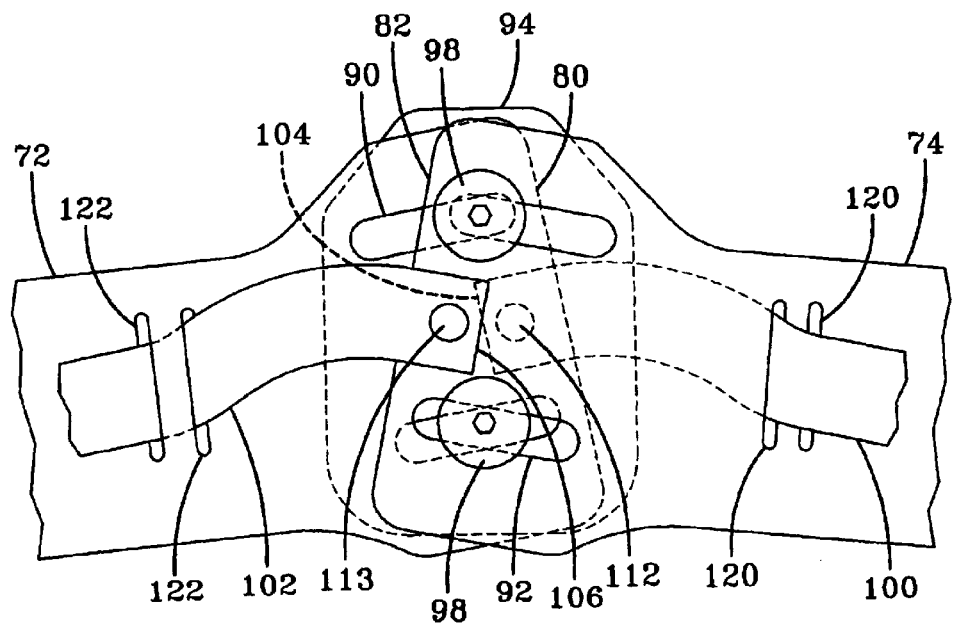
FIGS. 27 and 28 are partial rear elevational views of the orthosis shown in FIGS. 20–26 illustrating the rotational adjustment capability of the side segments relative to one another when necessary to adapt to a wearer's torso shape.
Figure 28:
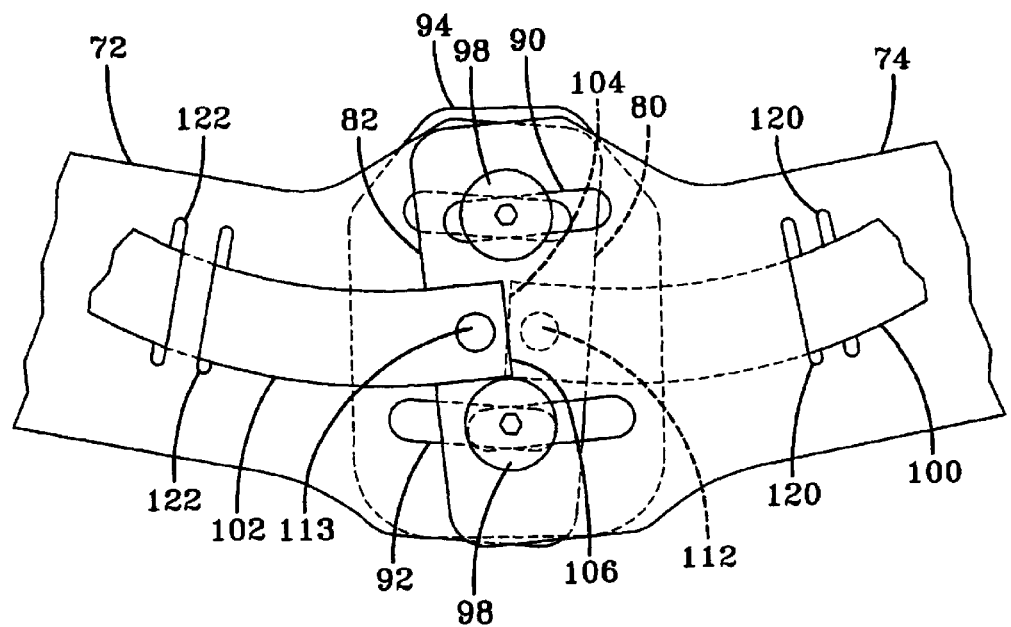

Further, as illustrated in FIGS. 27 and 28, the construction of the orthosis of the present invention with respect to the moveable relationship between the fasteners 98 and slots 90 and 92 permit each segment a degree of rotational adjustment about fasteners 98. This is particularly convenient if the wearer's body shape relative to the waist area and upper hip area covered by segments 72 and 74 differ in circumference. Each segment has a degree of freedom to permit the upper and lower slots of each segment to be rotated about fasteners 98 such that the effective circumference between the upper and lower portions of each segment may vary relative to one another to adjust to the variance in the circumference of the wearer in these areas.

For the majority of users, the difference in torso girth covered by the segments would not vary to a significant degree, however, this feature provides for a better fit and is particularly helpful for body shapes which exhibit a significant difference in girth over the area surrounded by the segments 72 and 74.

In view of the foregoing description, the lumbar sacral orthosis represented by the present invention provides a firm, non-elastic trunk support which is easily adjustable to a given fit and degree of compression desired by the wearer. This non-elastic support provided is significantly more effective than that provided by orthosis having an elastic nature. Yet, the construction of the slidable connection between the posterior edges of the side segments and the rigid or semi-rigid posterior panel and the secondary tightening provided by straps 100 and 102 provide a great range of adaptability to the user which is adjustable not only to the wearer's girth, but also to an enhanced and adjustable measure of support in an easy to manufacture, relatively low cost orthotic device. Further, this high quality support does not require custom fitting by a trained technician.

While certain preferred embodiments of the present invention have been disclosed in detail, it is to be understood that various modifications may be adopted without departing from the spirit of the invention or scope of the following claims.

What is claimed is:

1. A lumbar-sacral orthosis comprising in combination,
   a) a main body including a left and right side belt segment of flexible, inelastic material configured to wrap around a wearer's torso in opposite directions relative to one another, each of said segments having an anterior edge extending in overlapping relationship to the anterior edge of the other segment over a frontal area of the wearer's waist and a posterior edge overlapping the posterior edge of the other segment generally over the wearer's lumbar spine;
   b) fastening means carried by each of said segments near each of said anterior edges for releasably fixing a front portion of said segments to one another over the wearer's abdominal area;
   c) at least two vertically spaced, horizontally extending slots provided in each of said segments and disposed near, but spaced from the respective posterior edges of a respective segment in a position wherein a respective one of said at least two horizontally extending slots of one of said segments are disposed in at least partially overlying relationship to a respective one of said at least two horizontally extending slots of the other of said segments;
   d) a discrete, at least semi-rigid lumbar support panel including at least two vertically spaced openings, said panel being disposed in juxtaposition to a portion of each of said segments with a respective one of said openings aligned with a respective one of said horizontally extending slots in a respective one of said segments;
   e) at least two fasteners, a respective one of said fasteners extended through a respective one of said horizontally extending slots in each of said segments and a respective one of said aligned openings in said lumbar support panel adjustably connecting the posterior edges of said side segments to said lumbar support panel to permit relative movement of said posterior edges toward or away from one another.

2. The orthosis defined in claim 1 further including a pair of straps having a fixed end and a free end, said fixed end of one of said straps being attached to said left side segment near but spaced from its posterior edge with its free end extending across said lumbar panel toward the anterior edge of said right side segment and releasably fixed to said right side segment, the fixed end of the other of said pair of straps being attached to said right side segment near but spaced from its posterior edge with its free end extending across said lumbar panel toward the anterior edge of said left side segment and releasably fixed to said right side segment.

* * * * *